United States Patent
Franc et al.

(10) Patent No.: US 6,800,761 B1
(45) Date of Patent: Oct. 5, 2004

(54) FORM OF IRBESARTAN, METHODS FOR OBTAINING SAID FORM AND PHARMACEUTICAL COMPOSITIONS CONTAINING SAME

(75) Inventors: Bruno Franc, Saze (FR); Christian Hoff, Saint Laurent des Arbres (FR); San Kiang, Madison, NJ (US); Mark D. Lindrud, Basking Ridge, NJ (US); Olivier Monnier, Villeveyrac (FR); Chenkou Wei, Princeton Junction, NJ (US)

(73) Assignee: Sanofi-Synthelabo, Paris (FR)

(*) Notice: Subject to any disclaimer, the term of this patent is extended or adjusted under 35 U.S.C. 154(b) by 0 days.

(21) Appl. No.: 09/720,017
(22) PCT Filed: Jun. 10, 1999
(86) PCT No.: PCT/FR99/01372
§ 371 (c)(1),
(2), (4) Date: Mar. 12, 2001
(87) PCT Pub. No.: WO99/67236
PCT Pub. Date: Dec. 29, 1999

(30) Foreign Application Priority Data

Jun. 24, 1998 (FR) .............................................. 98 08037

(51) Int. Cl.⁷ ............................................ C07D 403/10
(52) U.S. Cl. ....................................................... 548/253
(58) Field of Search ......................................... 548/253

(56) References Cited

U.S. PATENT DOCUMENTS

| | | |
|---|---|---|
| 5,270,317 A | 12/1993 | Bernhart et al. |
| 5,352,788 A | 10/1994 | Bernhart et al. |
| 5,559,233 A | 9/1996 | Bernhart et al. |
| 5,629,331 A | 5/1997 | Caron et al. |

FOREIGN PATENT DOCUMENTS

| | | |
|---|---|---|
| EP | 0 708 103 | 4/1996 |
| WO | WO 91/14679 | 10/1991 |

OTHER PUBLICATIONS

M. Bauer et al., J. Chem. Soc., Perkin Trans. 2, No. 2, pp. 475–481, 1998.
Chemical Abstracts, vol. 129, No. 6, Aug. 10, 1998, Abstract No. 74251.

*Primary Examiner*—Fiona T. Powers
(74) *Attorney, Agent, or Firm*—Michael D. Alexander; Paul E. Dupont

(57) ABSTRACT

The invention relates to a novel crystalline form of irbesartan, to pharmaceutical compositions containing it, to processes for preparing it, and to a method for treating cardiovascular diseases utilizing it.

6 Claims, 1 Drawing Sheet

SOLUBILITY AND METASTABLE ZONE LIMIT OF

IRBESARTAN FORM A IN ISOPROPANOL

Figure 1:
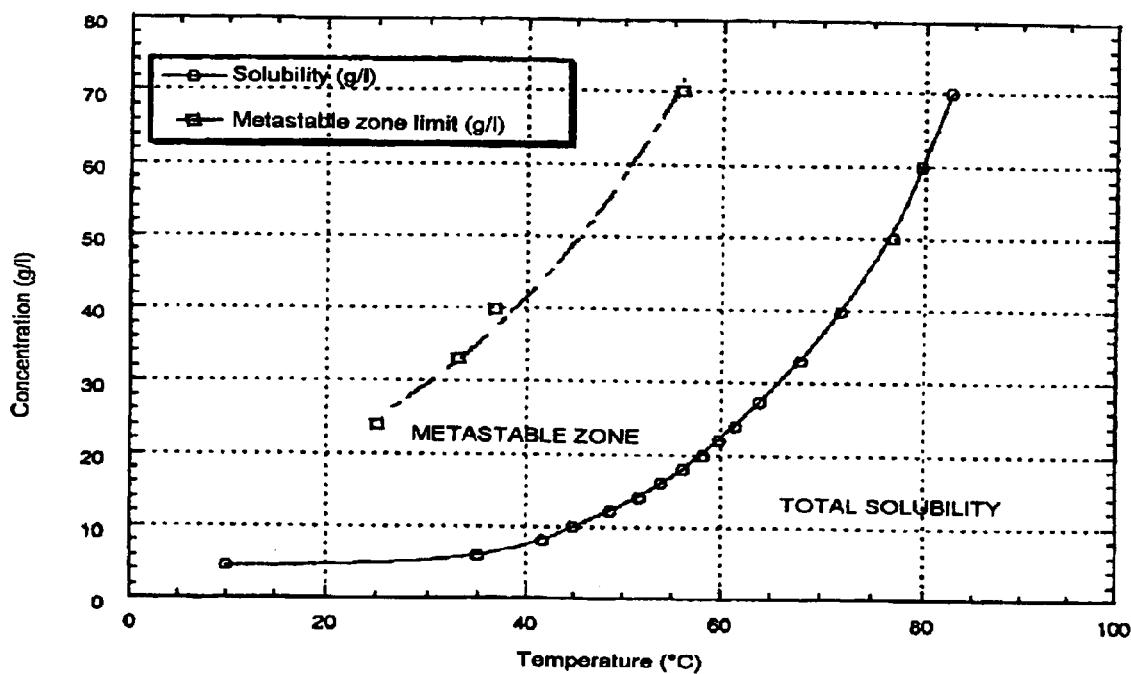

FORM OF IRBESARTAN, METHODS FOR OBTAINING SAID FORM AND PHARMACEUTICAL COMPOSITIONS CONTAINING SAME

This application is a 371 of PCT/FR99/01372 Filed Jun. 10, 1999.

The present invention relates to a novel crystal habit of 2-n-butyl-4-spirocyclopentane-1-[(2'-(tetrazol-5-yl)biphenyl-4-yl)methyl]-2-imidazolin-5-one of formula:

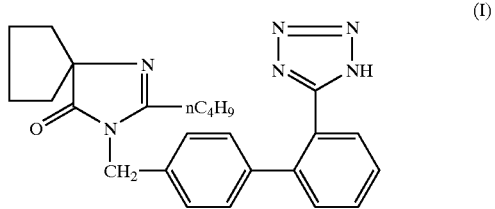

(I)

This compound and its method of preparation were disclosed for the first time in European patent EP 454 511. The compound of formula (I) is an angiotensin II antagonist which is useful in the treatment of cardiovascular diseases such as hypertension, cardiac insufficiency, cardiac arrhythmia, in the treatment of diseases of the central nervous system, in the treatment of glaucoma and diabetic retinopathy and in the treatment of renal insufficiency and diabetic nephropathy.

The common name of the compound of formula (I) is irbesartan and the term irbesartan is used in this description and in the claims to refer to the compounds of formula (I).

European patent application EP 708 103 discloses the existence of 2 crystalline forms of irbesartan:

one, known as form A, is the one obtained by crystallization in a solvent containing less than about 10% by volume of water, the other, known as form B, is obtained by crystallization in a water-miscible solvent containing more than about 10% water.

Each of these two forms is characterized by a specific X-ray diffraction profile.

Patent application EP 708 103 discloses that form B is a tautomeric form.

Patent application EP 708 103 indicates that irbesartan in the form A is in the form of stable, non-hygroscopic needles of high electrostatic nature. Hereinbelow in the present description, the term "acicular habit" denotes this crystalline form of the irbesartan form A.

It also been found that these crystals of acicular habit are difficult to filter and to dry and that they display poor flowability.

A novel crystal habit of the form A has now been found, characterized in that the ratio between the length and the width of the crystals is between 1:1 and 10:1, preferably between 1:1 and 5:1. This novel crystal habit of the form A of irbesartan will be defined by the term "brick habit" of irbesartan hereinbelow in the present description.

A subject of the present invention is also processes for obtaining irbesartan crystals of form A which have the novel crystal habit according to which the ratio between the length and the width of the crystals is between 1:1 and 10:1, preferably between 1:1 and 5:1.

The higher this ratio, the longer are the needles relative to their width, and thus an improvement in this ratio means a decrease of the said ratio. It is preferable for this ratio to decrease such that it is between 1:1 and 10:1, preferably between 1:1 and 5:1.

The improvement of this ratio means that the crystals have less of a tendency to break or to aggregate when they are wet, they can be filtered and dried faster, and they are easier to handle when they are dry.

The processes according to the invention have no effect on the polymorphism.

The irbesartan crystals in the brick habit have the physicochemical characteristics described below.

The powder X-ray diffraction profile (diffraction angle) was established with a Siemens D 550 TT diffractometer, and the significant lines are given in Table I below:

TABLE I

| d | $I/I_0$ |
|---|---|
| 11.22 | 100.00 |
| 7.90 | 12.02 |
| 7.52 | 13.79 |
| 7.23 | 18.60 |
| 6.27 | 20.14 |
| 6.09 | 6.47 |
| 5.86 | 7.42 |
| 5.60 | 98.76 |
| 5.41 | 19.45 |
| 5.05 | 24.67 |
| 4.97 | 20.36 |
| 4.91 | 12.92 |
| 4.80 | 27.33 |
| 4.61 | 15.90 |
| 4.49 | 14.73 |
| 4.36 | 9.86 |
| 4.17 | 62.84 |
| 4.07 | 15.39 |
| 3.97 | 30.34 |
| 3.88 | 14.32 |
| 3.83 | 13.56 |
| 3.75 | 37.28 |
| 3.53 | 26.48 |
| 3.46 | 12.42 |
| 3.40 | 27.88 |
| 3.27 | 11.03 |
| 3.18 | 10.42 |
| 3.15 | 7.28 |
| 3.12 | 6.11 |
| 3.05 | 15.50 |
| 3.01 | 9.49 |
| 2.81 | 7.11 |
| 2.78 | 9.40 |

This diffraction profile is that of the form A of irbesartan disclosed in EP 708 103.

The chargeability of the powder is measured by tribogeneration: the powder is subjected to a strong vibration during which it becomes charged on itself, and is then transferred into a Faraday cage connected to a very sensitive electrometer. The chargeability measured varies between 0 and −10 nanocoulomb/g. By way of comparison, the crystals of irbesartan in acicular form A have a chargeability, measured by the same process, of between −30 and −40 nanocoulomb/g.

The packing density of the irbesartan crystals having the new crystal habit, measured using a Hosokawa machine (180 gravity drops), is about 0.5 kg m$^3$, whereas that of the crystals of the acicular form A is about 0.35 kg/M$^3$.

The flowability index is calculated by the Carr method (R. Carr: Chemical Engineering, Jan. 18, 1965, page 163–168) and takes into account the results of four experimental values: compressibility, angle of repose, spatula angle and cohesion. This index is about 30 for the crystals of brick habit, whereas it is about 10 for the crystals of acicular habit.

It is found that the resistivity, the minimum inflammation energy, the minimum inflammation temperature, the results of the friction test and gravity of the explosion, measured in a 20-liter sphere, are similar for the two crystal habits of the form A of irbesartan.

The fact that the irbesartan crystals of brick habit are of reduced chargeability, i.e. they have a reduced tendency to store electrostatic charges, means that these crystals can be handled more easily and more safely.

The 50% increase in the packing density and in the flowability index of the brick habit with respect to the acicular habit represents an improvement which is reflected both in the chemical processability of the product and in their use for their preparation of pharmaceutical forms.

According to the present invention, the irbesartan of brick habit can be prepared using a process characterized in that a crystalline suspension of irbesartan of acicular habit form A is subjected to at least one sonication episode and at least one temperature oscillation episode.

Thus, the sonication episode can be either followed or preceded by the temperature oscillation episode.

It is also possible to envisage the sonication episode being carried out simultaneously with the temperature oscillation episode. According to the invention, a sonication episode can also be carried out between 2 phases of temperature oscillation.

Furthermore, the sonication and/or temperature oscillation episodes can be repeated independently of each other.

Preferably, a sonication episode is preceded by a temperature oscillation episode and more particularly a sonication episode is carried out between 2 temperature oscillation episodes.

The term "crystalline suspension" used in the present description refers to an irbesartan suspension prepared according to methods that are known to those skilled in the art. For example, the crystalline suspension can be prepared by growing irbesartan crystals in an organic solvent, for example an alcohol such as isopropanol, to prepare a supersaturated irbesartan solution, and cooling to a temperature at which the supersaturation is between 0% and 50%. The supersaturated solution is then seeded with 1% to 10% of irbesartan seed crystals of brick habit, the seed crystals originating from a previous batch. However, the seeds may also be generated by repeatedly subjecting the crystalline suspension to temperature oscillation and sonication episodes until crystals of brick habit are obtained. The seeded solution is then cooled to room temperature to form the crystalline suspension. The said crystalline suspension is then used according to the invention.

According to the present invention, a sonication episode consists in subjecting the crystalline suspension to a sonication energy whose frequency is from about 16 kHz to 10 MHz. It appears that the sonication episode limits the growth according to the length of the needles by breaking them and modifies the nature of the crystal surfaces such that the zones capable of accumulating the electrostatic charges are reduced. Sonication methods may be used either batchwise or semi-continuously or continuously.

For the batchwise sonication, an ultrasound probe is inserted into the crystalline suspension placed in a crystallizer.

The sonication episode can also be carried out continuously or semi-continuously by pumping the crystalline irbesartan suspension through a sonication cell at a flow rate of from about 10 liters/min/KW to liters/min/KW; with a pressure of from 0 psig to 100 psig; with an energy of about from 10 000 joules/liter to 30 000 joules/liter and at a frequency of about from 16 kHz to 10 MHz. Preferably, the flow rate is between 16 liters/min/KW and 18 liters/min/KW; the pressure is between 0 psig and 20 psig; the energy is between 16 000 and 25 000 joules/liter and the frequency is about 20 kHz.

The above sonication parameters such as the flow rate, the pressure and the frequency vary as a function of the expected result in terms of ratio between the length and the width of the crystals prepared.

The temperature oscillation episode comprises a heating phase and a cooling phase. According to the invention, it comprises at least one heating phase and at least one cooling phase in any order. It is preferable for a heating phase to be combined with a cooling phase, and even for the said heating phase to precede the said cooling phase. It is probable that the temperature oscillation contributes towards controlling the correct distribution of the size of the particles; in particular, it tends to dissolve the finer particles and to make the coarser particles grow.

The temperature oscillation is carried out by heating and cooling a crystalline suspension to predetermined temperatures. The heating phase is performed by heating up to about 20° C. to 100° C. Preferably, the heating phase is carried out at a temperature such that about 15% to 25% is dissolved in 60 minutes, more particularly about 20% of the crystals are dissolved in 60 minutes. The cooling phase of the temperature oscillation episode is generally carried out between 100° C. and −20° C. Preferably, the cooling phase is carried out at a temperature of between −5° C. and 20° C. for about 0 to 60 minutes; more particularly between 0 and 5° C. for about 0 to 60 minutes.

It should be noted that the temperature selected for the cooling phase of the temperature oscillation episode is less than the temperature selected for the corresponding heating phase. The heating and cooling phases can be repeated independently, as many times as necessary, and the specific parameters may be modified to obtain the desired product.

For example, it is possible to extend the heating phase and shorten the cooling phase to generate shorter crystals or alternatively it is possible to shorten the heating phase and extend the cooling phase to generate larger crystals. The number of heating and cooling phases also depends on the desired result. In general, if the number of heating and cooling phases increases, the appearance of the crystals improves and the ratio between the length and the width tends towards 1:1.

Controlling the sonication and temperature oscillation parameters makes it possible to control the size distribution of the particles and the ratio between the length and the width of the final crystals.

The process described above for modifying the crystal habit of irbesartan using sonication presents difficulties in industrial implementation. Specifically, the efficacy of the ultrasound emitter decreases beyond a few centimetres from the said emitter; furthermore, when working continuously, this efficiency decreases if the speed of passage of the crystalline suspension treated increases.

Also, to treat large volumes, the application time is very long. Moreover, high-power ultrasound causes premature wear of the metals and welds of the apparatus used.

Another process for modifying the crystal habit of the irbesartan form A uses wet grinding, i.e. the mechanical shearing of the crystals of acicular habit to convert them into crystals of brick habit. This process has the advantage of being readily applicable to the treatment of industrial amounts of product.

Thus, according to another of its aspects, the present invention relates to a process for preparing irbesartan of brick habit, characterized in that it contains the steps consisting in:

a) preparing a solution of irbesartan form A in an alcohol, under concentration and temperature conditions which allow the total solubility of the irbesartan;

b) cooling the said solution to a temperature selected as a function of the concentration of the solution, such that the solution is in the metastable zone;

c) seeding with irbesartan crystals of brick habit;

d) cooling the irbesartan solution to a temperature of between about 20° C. and 5° C.;

e) subjecting the crystalline suspension thus formed to a mechanical shearing using a shearing machine;

f) heating the crystalline suspension to a temperature of between about 40° C. and 60° C. to dissolve the fine particles;

g) cooling the crystalline suspension to a temperature of between about 20° C. and 5° C.;

h) filtering off the crystals of brick habit thus formed.

According to the present invention, a solution of irbesartan in alcohol, for example ethanol or, preferably, isopropanol, is used.

FIG. 1 indicates, for a solution of irbesartan form A in isopropanol, the conditions for total solubility, as a function of the concentration in g/liter and of the temperature in ° C. It also indicates the limits of the metastable zone for a solution containing 25 g/liter to 70 g/liter of irbesartan.

Thus, for a solution of irbesartan in isopropanol containing about 50 g/liter to 70 g/liter, the seeding temperature ranges from 45° C. to 80° C. in order for the solution to remain in the metastable zone.

The irbesartan solution can be seeded with irbesartan crystals of brick habit at any point in the cooling of the solution, when this solution is in the metastable zone. The seeding temperature is between 25° C. and 80° C., depending on the concentration of the solution. The proportion of seed crystals incorporated may be between 1% and 25%, preferably between 10% and 20%. After seeding, the temperature can be kept constant for a period of between a few minutes and 2 hours, preferably for half an hour to one hour.

In steps b) and d), the cooling is advantageously carried out at a uniform cooling rate of about 5° C. to 20° C. per hour, preferably in the region of 10° C. per hour.

In step e), the mechanical shearing is preferably carried out with a machine having a spin speed of about 10 000 to 15 000 rpm.

Machines having such characteristics are, for example, of the Turrax® type, sold by IKA-Werke (Germany). Some of these machines are suitable for treating industrial amounts ranging up to the point of allowing a flow rate of 100 m$^3$/hour. For the process according to the invention and at an industrial stage, a flow rate of between about 500 liters/hour and 4 m$^3$/hour is preferred, in a 2 m$^3$ reactor.

The mechanical shearing in step e) can be carried out either by placing the shearing machine in the reactor containing the crystalline suspension, or by passing the crystalline suspension continuously into the shearing machine. In this case, the flow rate of the machine is adjusted as a function of the ratio between the length and the width which is desired for the crystals of brick habit formed.

Optionally, in order to improve the yield of crystals of brick habit, steps e), f) and g) can be repeated before filtering off the crystals of brick habit formed and drying them.

A subject of the present invention is also pharmaceutical compositions containing, as active principle, irbesartan of brick habit, i.e. irbesartan of form A, having a novel crystal habit. These pharmaceutical compositions may be prepared according to the discription of patent application EP 747 050.

The formulations prepared with the brick habit can contain up to about 80% by weight of irbesartan or about 85% by weight of irbesartan combined with a diuretic agent, for example hydrochlorothiazide. These formulations may be prepared industrially, for example in the form of tablets or gel capsules, according to known processes, for example by wet granulation, dry granulation or direct tabletting.

By tabletting, tablets of uniform weight are obtained continuously, these tablets having physical properties that are suitable for industrial development.

EXAMPLE 1

A Preparation of Irbesartan Form A.

Irbesartan is prepared according to the procedure disclosed in European patent EP 454 511.

1) 2-n-butyl-4-spirocyclopentane-2-imidazoline-5-one

Ethyl amino-1-cyclopentanecarboxylate is prepared according to Adkins and Billica (J. Amer. Chem. Soc., 1948 70, 3121).

Ethyl valerimidate is prepared according to Mac Elvain (J. Amer. Chem. Soc., 1942, 64, 182–1827) and is then released from its hydrochloride by the action of potassium carbonate and extraction with methylene chloride.

Ethyl amino-1-cyclopentanecarboxylate (1.57 g) and ethyl valerimidate (1.56 g) are dissolved in 12 ml of xylene containing 6 drops of acetic acid. After refluxing for six and a half hours, the reaction medium is concentrated under vacuum and the residue is then chromatographed on silica gel, eluting with a chloroform/methanol/acetic acid mixture (94/4/2; v/v/v). The fraction containing the expected product is evaporated several times in the presence of xylene and then of benzene to remove the acetic acid. 1.91 g of product are obtained in the form of a thick oil.

IR (CHCl$_3$): 1720 cm$^{-1}$: C═O; 1635 cm$^{-1}$: C═N.

Comment: the fact that no band is observed between 1500 and 1600 cm$^{-1}$ indicates that, in the chloroform solution, the product is an imidazolin-5-one.

NMR spectrum: 0.92 ppm:t: 3H: C$\underline{H}_3$ (nBu); 1.35 ppm: sext: 2H: CH$_3$C$\underline{H}_2$—. 1.50–1.93 ppm: m: 10H: CH$_3$—CH$_2$—C$\underline{H}_2$ and cyclopentane; 2.33 ppm: t: 2H: CH$_3$—CH$_2$—CH$_2$—C$\underline{H}_2$—; 10.7 ppm: m: N$\underline{H}$.

Mass spectrum: MH$^+$: 195.

The 2-n-butyl-4-spirocyclopentane-2-imidazolin-5-one prepared in step A can also be obtained according to another procedure described below, using cyclopentanone as starting material.

i) 1-aminocyclopentanenitrile

This step is carried out according to A. Strecker (Org. Synth., 1955, 3).

1.97 g of sodium cyanide are dissolved in 3.9 ml of water in a round-bottomed flask and a solution containing 2.33 g of ammonium chloride in 5.9 ml of water and 3.5 ml of 20% aqueous ammonia is added, and 3 g of cyclopentanone in 3.8 ml of methanol are finally added to the flask. After stirring for 1 and a half hours, the mixture is maintained at 60° C. for 45 minutes and heating is then stopped, stirring is continued for 45 minutes and the mixture is then cooled to 25° C. It is extracted several times with methylene chloride. The extracts are dried over sodium sulfate, filtered and concentrated under vacuum. 4 g of the expected product are obtained in oily form.

The 1-aminocyclopentanenitrile obtained is dissolved in 300 ml of acetone and a solution of 2.25 g of oxalic acid dihydrate in 200 ml of acetone is added, with stirring. The precipitate formed is spin-filtered, washed with acetone and then dried.

m=4.71 g.

m.p.=220° C.

This compound is 1-aminocyclopentanenitrile hemioxalate.

ii) 1-aminocyclopentaneacetamide.

This step is carried out according to J. Zabicky, (The Chemistry of Amides, Intersciences, New York, 1970, 119).

5.1 g of the oxalate obtained in the preceding step are treated with 7.65 ml of concentrated sulfuric acid (d=1.84) for 45 minutes with stirring. An evolution of gas is observed and the temperature increases to 100° C. The mixture is cooled to about 35° C. and is poured into an ice/concentrated aqueous ammonia mixture (10 g/2.8 ml). The suspension formed is extracted 6 times in succession with chloroform containing 5% methanol. 3 ml of aqueous ammonia (d=0.92) is added to the aqueous phase and extraction is repeated with chloroform containing methanol (1/0.5; v/v). The combined organic phases are dried over sodium sulfate, filtered and concentrated. The expected product is obtained in the form of a white solid.

m=3.79 g m.p.=95° C.

The results of the analysis and the IR spectrum confirm the structure.

iii) 2-n-butyl-4-spirocyclopentane-2-imidazolin-5-one.

This step is performed according to H. Takenaka et al., Heterocycles, 1989, 29, (6), 1185–89.

3 g of the compound prepared in the preceding step are placed in 70 ml of anhydrous THF and 3.3 ml of triethylamine, and 3 ml of valeryl chloride in 10 ml of anhydrous THF are added with stirring. A white suspension forms. The intermediate compound formed, but not isolated, is (N-valeryl)-1-aminocyclopentanecarboxamide. 6 g of potassium hydroxide pellets, 7 ml of water and 16 ml of methanol are added. The mixture is refluxed for 2 and a half hours, followed by addition of 9 g of ammonium chloride. After stirring this mixture for 15 minutes, it is concentrated under vacuum. The residue obtained is taken up in 40 ml of water and extracted with 10 ml of ethyl acetate and then with twice 5 ml of ethyl acetate. The combined organic phases are dried over sodium sulfate and filtered. The filtrate is concentrated to dryness. 4.85 g of the expected product are obtained. The NMR spectrum is similar to that described above. The hydrochloride of this compound can be prepared by adding concentrated hydrochloric acid. The hydrochloride melts at 240° C. with sublimation.

2) 1-[(2'-Cyanobiphenyl-4-yl)methyl]-2-n-butyl-4-spirocyclopentane-2-imidazolin-5-one.

A mixture containing 250 mg of sodium hydride (as an 80% dispersion in mineral oil) and 5 ml of DMF is prepared under a nitrogen atmosphere, and a solution containing 0.97 g of 2-n-butyl-4-spirocyclopentane-2-imidazolin-5-one in 10 ml of DMF is added dropwise. The mixture is stirred for 30 minutes at room temperature, followed by addition of a solution of 1.5 g of 4-bromomethyl-2-cyanobiphenyl in 10 ml of DMF. After stirring for 1 hour at room temperature, the DMF is evaporated off under reduced pressure and the residue is then taken up in ethyl acetate and the organic phase is washed with water and then dried over sodium sulfate, filtered and evaporated. The residue is chromatographed on silica gel, eluting with a DCM/ethyl acetate mixture (9/1; v/v). 1.68 g of the. expected product are recovered. m.p.=92–93° C.

3) 2-n-Butyl-4-spirocyclopentane-1-[2'-(triphenylmethyltetrazol-5-yl)biphenyl-4-ylmethyl]-2-imidazolin-5-one.

1.56 g of the above product, 2.6 g of tributyltin azide and 30 ml of xylene are refluxed for 66 hours. The xylene is then evaporated off and the residue is dissolved in 20 ml of DCM and 5 ml of THF, adding 0.8 ml of 10N sodium hydroxide and, after stirring for 30 minutes, 2.5 g of trityl chloride, and the mixture is left stirring for 26 hours. After evaporation of the solvents, the residue is taken up in ethyl acetate and washed with water, with a 3% potassium hydrogen sulfate solution and with water. The resulting solution is dried and evaporated. The residue is chromatographed on alumina, eluting with a hexane/ethyl acetate (9/1:v/v) mixture. 1.97 g of the expected product are obtained. m.p.=150–152° C.

4) 2-n-Butyl-4-spirocyclopentane-1-[(2'-(tetrazol-5-yl)biphenyl-4-yl)methyl]-2-imidazolin-5-one.

1.96 g of the product prepared in the above step are dissolved in 10 ml of methanol and 10 ml of THF. After cooling of the reaction medium to 5° C., 1.5 ml of 4N hydrochloric acid are added and the mixture is stirred for 3 hours at room temperature and for 1 hour at 30° C. After evaporation of the solvents, the residue is taken up in water and brought to pH 12 by addition of 10N sodium hydroxide. The aqueous phase is extracted with ether, with toluene and again with ether. The aqueous phase is acidified to pH 2 by addition of 1N hydrochloric acid and is then extracted with ethyl acetate, dried over $Na_2SO_4$ and evaporated. The white solid obtained is dried at 50° C. under 0.05 mm of mercury. 840 mg of the expected product are obtained. m.p.=180–181° C.

NMR spectrum: 0.75 ppm: t: 3H: $CH_3$ (nBu); 1.10 ppm: sext: 2H: $CH_3$—$\underline{CH}_2$—; 1.20 ppm: quint: 2H: $CH_3$—$CH_2$—$\underline{CH}_2$—; 1.5–2 ppm: m: 8H: —$C_5H_8$; 2.2 ppm: t: 2H: $CH_3$—$CH_2$—$\underline{CH}_2$; 4.6 ppm: s: 2H: $C\underline{H}_2$—$C_6H_4$—; 7 ppm: s: 4H: $CH_2$—$C_6\underline{H}_4$—; 7.35–7.7 ppm: m: 4H: $H_{3',4',5',6'}$ aromatic.

The N.O.E. study confirms the position of the 5-one substitution on the imidazole.

The crystals formed can be characterized by their X-ray diffraction spectrum (Table 1) and correspond to irbesartan form A.

| d | I/I$_0$ |
|---|---|
| 11.22 | 100.00 |
| 7.90 | 12.02 |
| 7.52 | 13.79 |
| 7.23 | 18.60 |
| 6.27 | 20.14 |
| 6.09 | 6.47 |
| 5.86 | 7.42 |
| 5.60 | 98.76 |
| 5.41 | 19.45 |
| 5.05 | 24.67 |
| 4.97 | 20.36 |
| 4.91 | 12.92 |
| 4.80 | 27.33 |
| 4.61 | 15.90 |
| 4.49 | 14.73 |
| 4.36 | 9.86 |
| 4.17 | 62.84 |
| 4.07 | 15.39 |
| 3.97 | 30.34 |
| 3.88 | 14.32 |
| 3.83 | 13.56 |
| 3.75 | 37.28 |
| 3.53 | 26.48 |
| 3.46 | 12.42 |
| 3.40 | 27.88 |
| 3.27 | 11.03 |
| 3.18 | 10.42 |
| 3.15 | 7.28 |
| 3.12 | 6.11 |
| 3.05 | 15.50 |

-continued

| d | I/I₀ |
|---|---|
| 3.01 | 9.49 |
| 2.81 | 7.11 |
| 2.78 | 9.40 |

The crystals thus obtained can be recrystallized in the following way.

15 ml of isopropanol are added to 840 mg of the product obtained and the mixture is heated until dissolution is complete. The solution is cooled to room temperature and the crystals formed are then filtered off, washed with water and dried. 805 mg of irbesartan form A are obtained.

B Preparation of the Seed Crystals.

The crystals subsequently used as seeds are prepared according to the following procedure.

Cycle I

A three-necked round-bottomed flask fitted with a mechanical stirrer is loaded with 200 ml of isopropyl alcohol and 9.40 g of the compound obtained in step A. The crystalline suspension is heated at 77.0° C., with stirring (about 100 rpm), until dissolution is complete. The solution is cooled to 73.0° C. and a further 0.09 mg of the compound from step A is added to initiate the crystallization. The crystalline suspension is cooled to 20.0° C. over 20 minutes. The suspension is subjected to sonication for 600 seconds at a power of 10–15 watts, using a 0.63 cm O.D. sonication probe.

Cycle II.

The crystalline suspension is heated to 74.0° C., which dissolves about 93% of the crystals, leaving only the largest crystals for the next crystallization.

The mixture is cooled to 20.0° C. over 180 minutes according to the cubic temperature decrease described below:

| Time, minutes | Temperature, ° C. |
|---|---|
| 0 | 74.0 |
| 30 | 73.8 |
| 60 | 72.0 |
| 90 | 67.3 |
| 120 | 58.0 |
| 150 | 42.8 |
| 180 | 20.0 |

When the temperature of 20.0° C. is reached, the reaction medium is subjected to sonication for 600 seconds at a power of 10–15 watts.

Cycle III.

The crystalline suspension is heated to 74.0° C. As in cycle II, it is cooled to 20.0° C. over 180 minutes, according to the cubic temperature decrease described above. When the temperature of 20.0° C. is reached, the crystalline suspension is subjected to sonication for 600 seconds at a power of 10 to 15 watts.

Cycle IV.

The crystalline suspension is heated to 74.0° C. As in cycle II, it is cooled to 20.0° C. over 180 minutes, according to the cubic temperature decrease described above. When the temperature of 20.0° C. is reached, the crystalline suspension is subjected to sonication for 600 seconds at a power of 10 to 15 watts.

Cycle V.

The crystalline suspension is heated to 74.0° C. As in cycle II, it is cooled to 20.0° C. over 180 minutes, according to the cubic temperature decrease described above. When the temperature of 20.0° C. is reached, the crystalline suspension is subjected to sonication for 600 seconds at a power of 10 to 15 watts.

Cycle VI.

The crystalline suspension is heated to 74.0° C. As in cycle II, it is cooled to 20.0° C. over 180 minutes, according to the cubic temperature decrease described above. The crystalline suspension is cooled to 5.0° C. and the product is filtered off on a Buchner funnel and dried under vacuum at 70° C. overnight to give the seed crystals.

C. Crystallization Procedure 515 g of the compound from step A are mixed with 10.95 liters of isopropanol to form the crystalline suspension. This is heated to 80° C. to dissolve all of the solid. The crystalline suspension is then cooled to 20° C. according to the cubic temperature decrease described above, over 4 hours and with addition at 73° C. of 5.13 g of seed crystals, obtained in step B. A 1.27 cm O.D. sonication probe is introduced for 10 minutes at a power of 125 W. The solution is heated again to 73° C. to dissolve the small crystals and is then cooled to 20° C. over 4 hours according to the cubic temperature decrease described above.

The solution is then subjected to sonication for 10 minutes at a power of 125 W. The solution is heated again to 73° C. to dissolve the small crystals. The solution is cooled to 20° C., using the cubic temperature decrease described above, over 6 hours and the solution is then maintained at 2° C. for 1 hour. The reaction medium is filtered to form a wet filtrate. This is dried at 50° C. under vacuum overnight. 513.4 g of the dry product are obtained, having a width: length ratio of 1:2 to 1:5.

EXAMPLE 2

A) Preparation of the Solution of Irbesartan of Form A.

The process is performed according to the procedure described in Example 1, step A. 116 kg of irbesartan and 1585 l of isopropanol are loaded into a 2000 l reactor and the mixture is then refluxed for 30 minutes to obtain total dissolution. The solution is hot-filtered, to remove the insoluble particles, into another reactor, passing via a cartridge with a 0.6 μm cut-off threshold. The filtered solution is refluxed again to dissolve any seed crystals present, and is then cooled to 80° C. with stirring at about 50 rpm.

B) Preparation of the Seed Crystals.

The seed crystals are obtained in the laboratory in successive steps of heating and cooling of a solution of irbesartan form A in isopropanol, the solution undergoing a passage through the shearing machine (Turrax®) after each cooling.

C) Crystallization Procedure a) A suspension of seed crystals containing 17.4 kg in 33.1 of isopropanol is prepared and is introduced in a single portion into the solution prepared in step A and maintained at 80° C. for 1 hour. The temperature of the reactor is reduced to 20° C. at a uniform cooling rate of 10° C. per hour. A population of crystals is obtained whose length is 300 μm to 500 μm and whose width is 20 μm to 50 μm at the end of crystallization, i.e. a ratio of 25:1 to 6:1.

b) The crystalline suspension is treated for 35 minutes (flow rate of 4 m³/hour) in a Turrax® shearing machine, referenced IKA/DISPAX Reactor DRS 2/10, at a spin speed of 12 000 rpm. Crystals are obtained having a length of 40 μm to 110 μm and a width of 5 μm to 40 μm, i.e. a ratio of 8:1 to 1:1. Many fine particles are also present.

c) The temperature of the reactor is raised to 50° C. and this temperature is maintained for 1 hour to dissolve the fine particles.

d) The temperature of the reactor is reduced to 5° C. at a uniform cooling rate of 10° C. per hour and is then maintained at this temperature for one hour.

e) By filtration, a population of crystals of brick habit is obtained (average length 30 μm, average width 5 μm, ratio 6:1). After drying, 121 kg of crystals of brick habit with an isopropanol content of less than 1000 ppm are obtained.

| EXAMPLE 3 Tablet: percentage formulation | |
|---|---|
| Irbesartan of brick habit | 70 |
| Microcrystalline cellulose | 24.75 |
| Sodium croscarmellose | 3.75 |
| Hydrated colloidal silica | 0.75 |
| Magnesium stearate | 0.75 |
| EXAMPLE 4 Tablet: percentage formulation | |
| Irbesartan of brick habit | 70 |
| Microcrystalline cellulose | 12.375 |
| Sodium croscarmellose | 3.75 |
| Polyethylene glycol | 12.375 |
| Hydrated colloidal silica | 0.75 |
| Magnesium stearate | 0.75 |
| EXAMPLE 5 Tablet | |
| Irbesartan of brick habit | 75 mg |
| Hydrochlorothiazide | 12.50 mg |
| Microcrystalline cellulose | 7.75 mg |
| Sodium croscarmellose | 3.25 mg |
| Hydrated colloidal silica | 0.75 mg |
| Magnesium stearate | 0.75 mg |
| Per tablet | |
| EXAMPLE 6 Tablet | |
| Irbesartan of brick habit | 150 mg |
| Hydrochlorothiazide | 12.50 mg |
| Microcrystalline cellulose | 15.50 mg |

| -continued | |
|---|---|
| Sodium croscarmellose | 6.50 mg |
| Hydrated colloidal silica | 1.50 mg |
| Magnesium stearate | 1.50 mg |
| Per tablet. | |

What is claimed is:

1. A crystalline compound of formula:

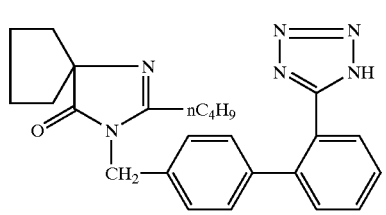

(I)

having a crystal habit such that the ratio between the length and the width of the crystals is between 1:1 and 10:1.

2. A crystalline compound according to claim 1, in which the ratio between the length and the width of the crystals is between 1:1 and 5:1.

3. A pharmaceutical composition comprising a compound according to claim 1 and pharmaceutically acceptable excipients.

4. A pharmaceutical composition according to claim 3 further comprising a diuretic agent.

5. A pharmaceutical composition according to claim 4, in which the diuretic agent is hydrochlorothiazide.

6. A pharmaceutical composition comprising a compound according to claim 2 and pharmaceutically acceptable excipients.

* * * * *